(12) United States Patent
Tieu et al.

(10) Patent No.: US 9,968,358 B2
(45) Date of Patent: May 15, 2018

(54) IMPLANT DELIVERY SYSTEM

(75) Inventors: Tai D. Tieu, Fountain Valley, CA (US); Hideo Morita, Irvine, CA (US); Helen Nguyen, Tustin, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 1245 days.

(21) Appl. No.: 12/761,187

(22) Filed: Apr. 15, 2010

(65) Prior Publication Data

US 2010/0268201 A1    Oct. 21, 2010

Related U.S. Application Data

(60) Provisional application No. 61/169,632, filed on Apr. 15, 2009.

(51) Int. Cl.

| | |
|---|---|
| *A61F 2/95* | (2013.01) |
| *A61B 17/12* | (2006.01) |
| *A61F 2/966* | (2013.01) |
| *A61F 2/24* | (2006.01) |
| *A61F 2/30* | (2006.01) |

(52) U.S. Cl.
CPC .... *A61B 17/12022* (2013.01); *A61B 17/1214* (2013.01); *A61F 2/95* (2013.01); *A61F 2/966* (2013.01); *A61B 2017/12054* (2013.01); *A61F 2/2439* (2013.01); *A61F 2002/30062* (2013.01);
(Continued)

(58) Field of Classification Search
CPC ................ A61F 2/95; A61F 2002/9505; A61F 2002/9511; A61F 2002/011; A61F 2/966; A61F 2/2439; A61F 2002/30062; A61F 2210/0004; A61M 2025/0004; A61M 2025/0006; A61B 2017/1205;
(Continued)

(56) References Cited

U.S. PATENT DOCUMENTS

| | | |
|---|---|---|
| 4,346,712 A | 8/1982 | Handa et al. |
| 5,108,407 A | 4/1992 | Geremia et al. |

(Continued)

FOREIGN PATENT DOCUMENTS

| | | |
|---|---|---|
| WO | WO 93/11825 | 6/1993 |
| WO | WO 03/101518 A1 | 12/2003 |

OTHER PUBLICATIONS

WIPO, U.S. International Search Authority, International Search Report and Written Opinion dated Jun. 8, 2010 in International Patent Application No. PCT/US2010/031268, 9 pages.

*Primary Examiner* — Anh Dang
*Assistant Examiner* — Erin Colello
(74) *Attorney, Agent, or Firm* — Inskeep IP Group, Inc.

(57) ABSTRACT

In one embodiment, the present invention relates to a mechanically releasable delivery system. More specifically, this embodiment includes an implantable device secured by tether at a distal end of the delivery system. The tether is fixed to the implantable device and looped around a selectively slidable mandrel. When the mandrel is retracted to expose its distal end, the looped tether slides off the mandrel, freeing the implantable device. Alternately, the tether can be fixed to the delivery system, wrapped around a portion of the implantable device and looped on to the slidable mandrel. Preferably, movement of the mandrel is controlled by an actuation control on the handle of the delivery system, allowing the user to selectively release the implantable device during a medical procedure.

20 Claims, 7 Drawing Sheets

(52) U.S. Cl.
CPC ............... *A61F 2002/9505* (2013.01); *A61F 2002/9511* (2013.01); *A61F 2210/0004* (2013.01)

(58) Field of Classification Search
CPC ........... A61B 2017/12054; A61B 2017/22049; A61B 2017/347; A61B 17/12022; A61B 17/1214
USPC .......................................... 606/200; 623/1.11
See application file for complete search history.

(56) References Cited

U.S. PATENT DOCUMENTS

| | | | | |
|---|---|---|---|---|
| 5,147,370 | A * | 9/1992 | McNamara et al. | 623/1.11 |
| 5,242,452 | A * | 9/1993 | Inoue | A61F 2/07 606/108 |
| 5,250,071 | A * | 10/1993 | Palermo | 606/198 |
| 5,261,916 | A * | 11/1993 | Engelson | 606/108 |
| 5,290,305 | A * | 3/1994 | Inoue | A61F 2/07 600/37 |
| 5,383,853 | A * | 1/1995 | Jung | A61M 25/0068 604/103.04 |
| 5,578,074 | A | 11/1996 | Mirigian | |
| 5,582,619 | A | 12/1996 | Ken | |
| 5,676,671 | A * | 10/1997 | Inoue | A61F 2/95 604/247 |
| 5,800,455 | A * | 9/1998 | Palermo | A61B 17/12022 606/108 |
| 5,895,385 | A | 4/1999 | Guglielmi et al. | |
| 5,925,059 | A * | 7/1999 | Palermo et al. | 606/191 |
| 5,964,771 | A * | 10/1999 | Beyar et al. | 606/108 |
| 6,048,338 | A * | 4/2000 | Larson | A61M 25/0054 604/523 |
| 6,165,178 | A * | 12/2000 | Bashiri et al. | 606/108 |
| 6,183,504 | B1 * | 2/2001 | Inoue | A61F 2/07 623/1.11 |
| 6,238,415 | B1 * | 5/2001 | Sepetka | A61B 17/12022 604/96.01 |
| 6,270,520 | B1 * | 8/2001 | Inoue | A61F 2/07 623/1.11 |
| 6,478,773 | B1 * | 11/2002 | Gandhi | A61B 17/12 604/113 |
| 6,500,149 | B2 | 12/2002 | Gandhi et al. | |
| 6,514,282 | B1 * | 2/2003 | Inoue | A61F 2/95 623/1.13 |
| 6,537,284 | B1 * | 3/2003 | Inoue | A61F 2/954 606/108 |
| 6,585,718 | B2 * | 7/2003 | Hayzelden | A61B 18/1492 138/118 |
| 6,602,261 | B2 | 8/2003 | Greene, Jr. et al. | |
| 6,740,073 | B1 | 5/2004 | Saville | |
| 6,966,892 | B2 | 11/2005 | Gandhi et al. | |
| 7,014,645 | B2 | 3/2006 | Greene, Jr. et al. | |
| 7,198,613 | B2 | 4/2007 | Gandhi et al. | |
| 7,367,987 | B2 * | 5/2008 | Balgobin et al. | 606/200 |
| 7,371,251 | B2 * | 5/2008 | Mitelberg et al. | 606/200 |
| 7,628,797 | B2 * | 12/2009 | Tieu et al. | 606/148 |
| 7,708,754 | B2 * | 5/2010 | Balgobin et al. | 606/200 |
| 7,708,755 | B2 * | 5/2010 | Davis, III | A61B 17/12022 606/191 |
| 7,811,305 | B2 * | 10/2010 | Balgobin | A61B 17/12022 606/191 |
| 8,034,094 | B2 * | 10/2011 | Aoba | A61F 2/94 623/1.11 |
| 8,142,455 | B2 * | 3/2012 | Thompson | A61B 17/12022 606/157 |
| 9,510,962 | B2 * | 12/2016 | Aoba | A61F 2/95 |
| 2001/0044633 | A1 * | 11/2001 | Klint | A61B 17/12022 606/200 |
| 2002/0173837 | A1 * | 11/2002 | Lauterjung | 623/1.12 |
| 2003/0023262 | A1 | 1/2003 | Welch | |
| 2003/0045901 | A1 | 3/2003 | Opolski | |
| 2004/0034363 | A1 * | 2/2004 | Wilson | A61B 17/12022 606/108 |
| 2005/0043755 | A1 | 2/2005 | Wilson et al. | |
| 2005/0154440 | A1 * | 7/2005 | Limon | A61F 2/958 623/1.11 |
| 2005/0171572 | A1 | 8/2005 | Martinez | |
| 2006/0052815 | A1 * | 3/2006 | Fitz | A61B 17/0057 606/200 |
| 2006/0116714 | A1 * | 6/2006 | Sepetka | A61B 17/12022 606/200 |
| 2006/0241684 | A1 | 10/2006 | Wilson et al. | |
| 2006/0241685 | A1 | 10/2006 | Wilson et al. | |
| 2006/0253149 | A1 * | 11/2006 | Gandhi | A61B 17/12 606/200 |
| 2006/0276826 | A1 * | 12/2006 | Mitelberg | A61B 17/12022 606/200 |
| 2006/0276829 | A1 * | 12/2006 | Balgobin et al. | 606/200 |
| 2006/0276834 | A1 * | 12/2006 | Balgobin | A61B 17/12022 606/200 |
| 2007/0010849 | A1 * | 1/2007 | Balgobin et al. | 606/200 |
| 2007/0055302 | A1 * | 3/2007 | Henry | A61B 17/12022 606/200 |
| 2007/0221230 | A1 * | 9/2007 | Thompson | A61B 17/12022 128/207.15 |
| 2007/0270903 | A1 * | 11/2007 | Davis, III | A61B 17/12022 606/200 |
| 2008/0045997 | A1 * | 2/2008 | Balgobin | A61B 17/12022 606/200 |
| 2008/0097462 | A1 * | 4/2008 | Mitelberg | A61F 2/95 606/108 |
| 2008/0119891 | A1 * | 5/2008 | Miles et al. | 606/213 |
| 2008/0133028 | A1 | 6/2008 | Wilson et al. | |
| 2008/0140111 | A1 | 6/2008 | Wilson et al. | |
| 2008/0147201 | A1 | 6/2008 | Wilson et al. | |
| 2008/0243218 | A1 * | 10/2008 | Bottomley | A61N 1/05 607/116 |
| 2008/0283066 | A1 | 11/2008 | Delgado et al. | |
| 2008/0306503 | A1 * | 12/2008 | Que | A61B 17/12022 606/191 |
| 2009/0082842 | A1 * | 3/2009 | Glynn | A61F 2/91 623/1.11 |
| 2011/0092997 | A1 * | 4/2011 | Kang | A61B 17/12022 606/191 |
| 2012/0065667 | A1 * | 3/2012 | Javois | A61B 17/12122 606/213 |

\* cited by examiner

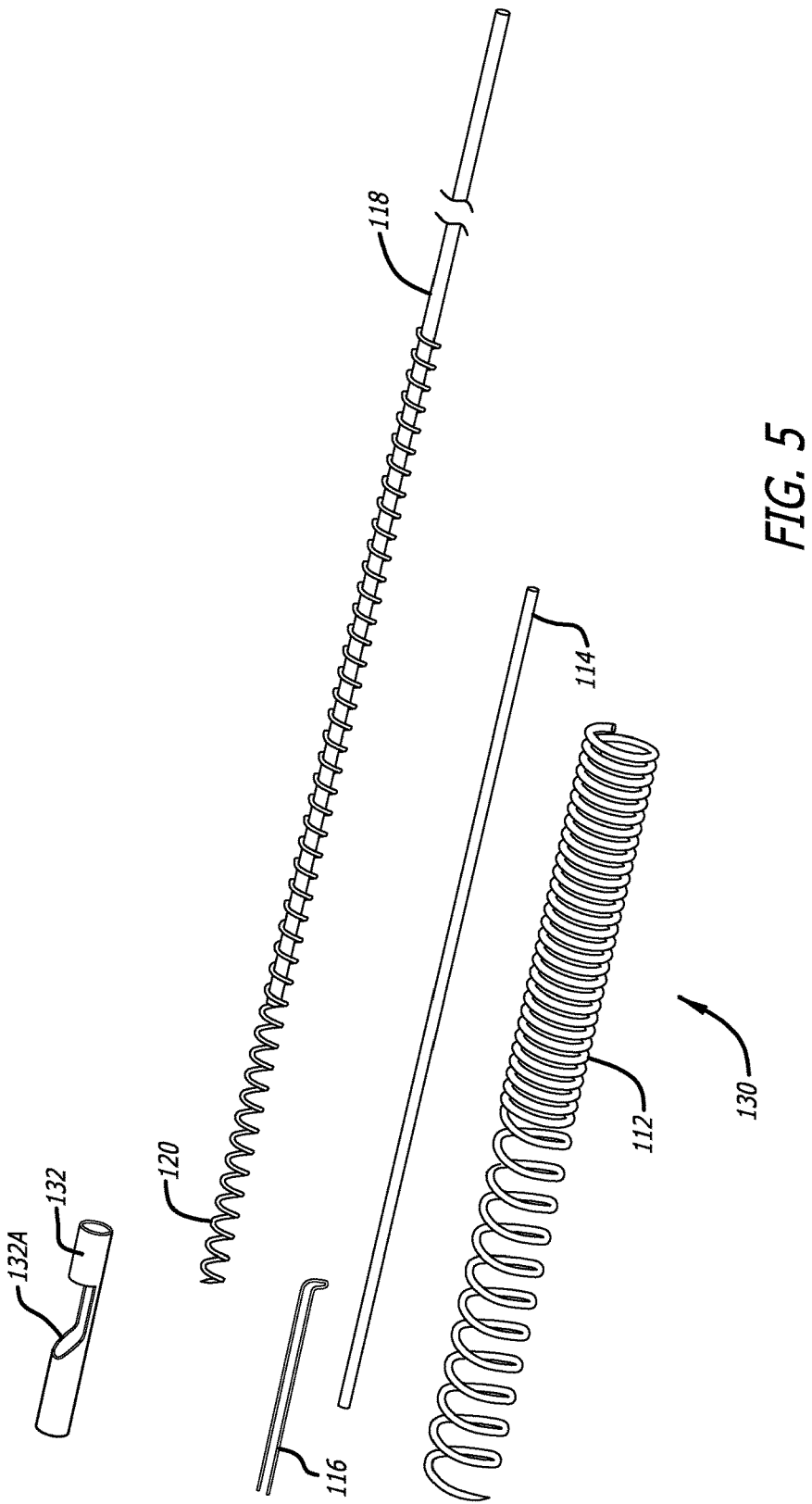

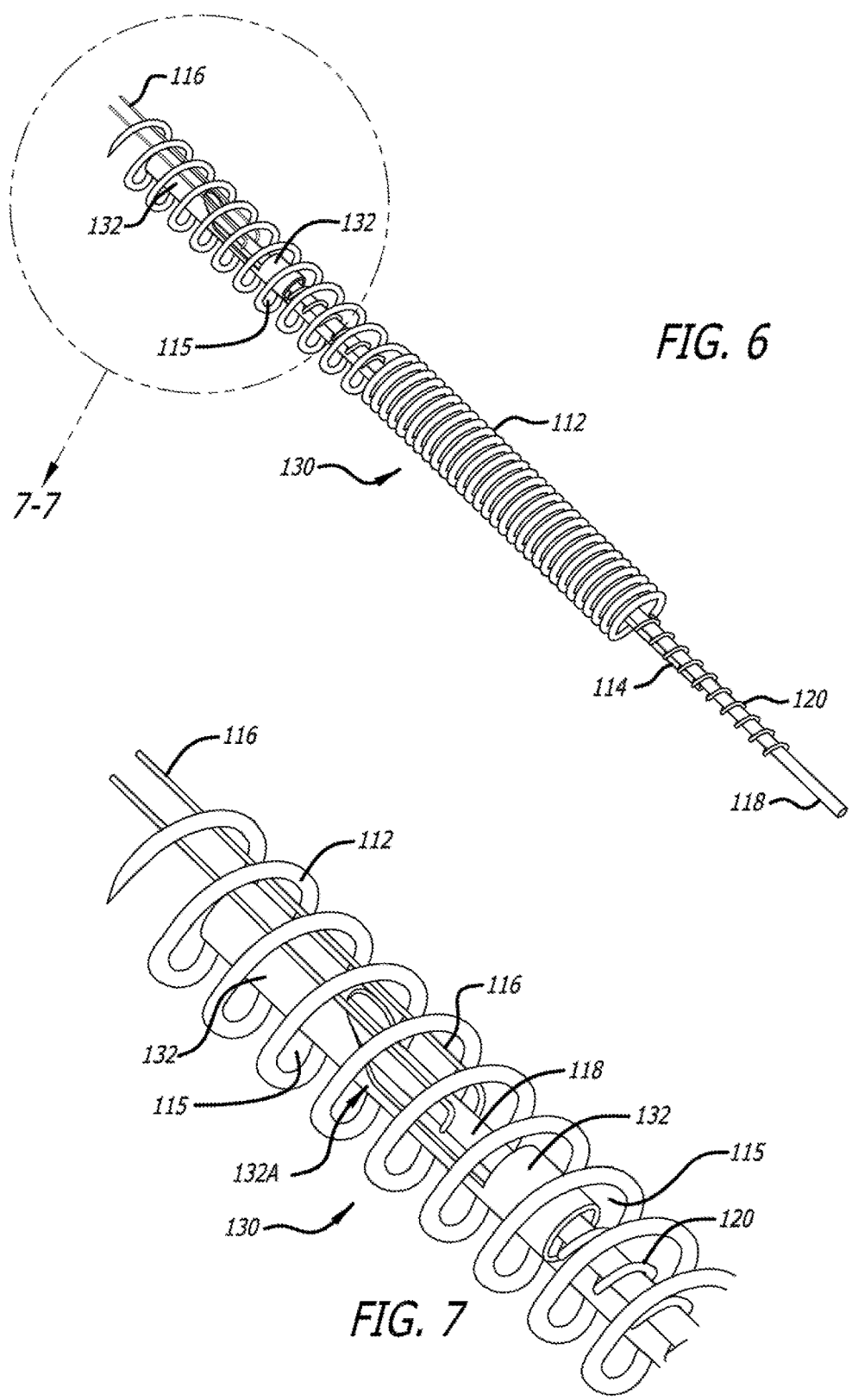

IMPLANT DELIVERY SYSTEM

RELATED APPLICATIONS

This application claims priority to U.S. Provisional Application Ser. No. 61/169,632 filed Apr. 15, 2009 entitled Implant Delivery System which is hereby incorporated by reference.

FIELD OF THE INVENTION

This invention relates to an improved delivery system for delivering an implantable medical device. More specifically, this invention relates to an implant delivery system with an improved implantable device release mechanism.

BACKGROUND OF THE INVENTION

Implantable medical devices and their accompanying delivery systems are well known in the art. These implantable devices include stents, microcoils, valves and similar types of devices which are used to treat a variety of different medical conditions.

Many implantable devices are delivered within a patient by way of a catheter-style delivery device. One type of delivery system commonly used with self-expanding implantable devices utilizes two concentrically arranged catheters or shafts. The implantable device is disposed axially around a distal end of the inner catheter or pusher and held in a compressed position by the outer sleeve. Once the implantable device is positioned at a target location, the outer shaft is withdrawn, releasing the implantable device at the target location.

One drawback often associated with this type of delivery system is the inability of the user to reposition the implantable device once released. In this respect, if the implantable device deploys in an undesirable position or configuration, the user is unable to recapture or otherwise reposition the device to a desired location. Curves in the path of the catheter through the human body can cause friction and further difficulties when evenly withdrawing the outer shaft and therefore can further result in undesirable device deployment.

Other deployment systems also typically include a mechanism for selectively uncoupling the implantable device from the delivery system. For example, some delivery systems for non-expandable implants include a tether fixed to both the delivery catheter and the implantable device. When the user wishes to release the implantable device, a nearby heater melts the tether, thereby releasing the device.

In such a delivery system, a portion of the melted tether remains on the implantable device. In some procedures, this tether remnant may cause complications in the patient such as blood clots, especially if located within a blood vessel. In other procedures, this tether remnant may pose less risk for complications and therefore may be of less concern to a physician.

There remains a need in the art for an implantable device delivery system that overcomes the drawbacks of the prior art.

SUMMARY OF THE INVENTION

One preferred embodiment according to the present invention relates to a mechanically releasable delivery system. More specifically, this embodiment includes an implantable device secured by a flexible tether at a distal end of the delivery system. The tether is fixed (e.g., a knot, adhesive, welding, etc.) to the implantable device and looped around a selectively slidable mandrel. When the mandrel is retracted to expose its distal end, the looped tether slides off the mandrel, freeing the implantable device. Alternately, the tether can be fixed to the delivery system, wrapped around a portion of the implantable device and looped on to the slidable mandrel. Preferably, movement of the mandrel is controlled by grasping the mandrel at a proximal end of the mandrel and sliding the mandrel in a proximal direction, thereby causing the implantable device to be released within the patient.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which:

FIG. 5 illustrates an exploded view of another preferred embodiment of a release mechanism according to the present invention;

FIG. 6 illustrates an assembled perspective view of the release mechanism of FIG. 5;

FIG. 7 illustrates an enlarged view of area 7-7 showing the release mechanism of FIG. 6;

DESCRIPTION OF EMBODIMENTS

Figure 1:
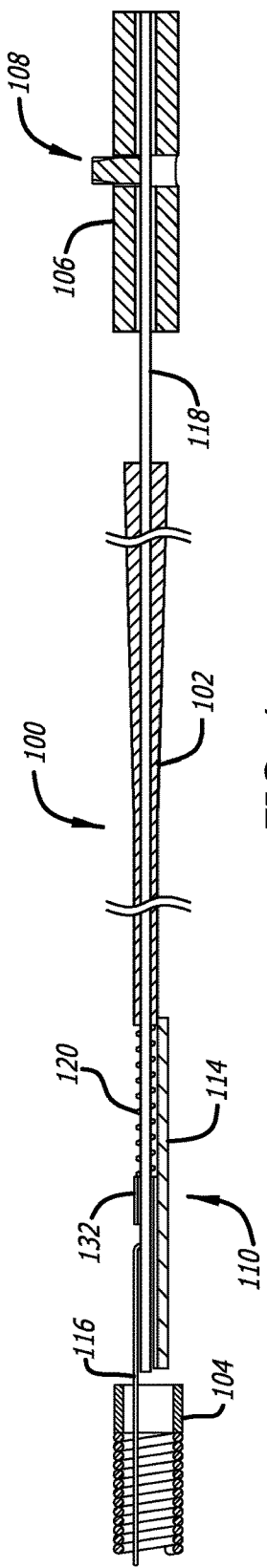
FIG. 1 illustrates a side view of a preferred embodiment of a delivery system according to the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 illustrates a preferred embodiment of a delivery system 100 according to the present invention. Preferably, the delivery system 100 includes an elongated body 102, such as a pusher body for advancing within a patient (e.g., within a pre-positioned catheter or with a retractable outer sheath).

The distal end of the delivery system 100 includes an implantable device 104 (e.g., stent, valve, microcoil, etc.). A proximal end of the delivery device 100 may include a grip or handle 106 for grasping the device 100 and advancing it into the patient. Preferably, an outer sheath is used to introduce a microcatheter to a desired target location. The delivery system is introduced into the microcatheter and advanced to the target location.

The proximal end of the delivery device 100 further includes an implantable device release control 108 which allows the user to cause the implantable device 104 to be released from the delivery system and left within the patient. More specifically, and as discussed in greater detail below, the release control 108 allows the user to retract (i.e., move proximally) a detachment mandrel 118 (i.e., an implant capture member, actuating member, or an elongated locking member). As a distal end of the detachment mandrel 118 retracts, it releases a flexible tether 116 that secures the implantable device 104 to the delivery system 100.

Preferably, the release control 108 is formed by the proximal end of the detachment mechanism which slides relative to the body 102 or the handle 106. A hypotube can be further included near or in the handle 106, through which the detachment mandrel 118 slides.

While the proximal end of the detachment mandrel 118 may simply be exposed to allow the user to move as desired, a wire can also be connected to the detachment mandrel 118, allowing a user to pull the wire and therefore pull the detachment mandrel 118 proximally. Further, the detachment mandrel 118 can be spring biased to a closed position, for example, by disposing a spring at a proximal end of the detachment mandrel 118, within the handle 106.

In other examples, this release control 108 may be a slider, lever, mechanical button, electrical button or any other type of actuation mechanism. The release mechanism 110 is preferably located within a passage of the body 102 near a distal end of the body 102.

Figure 2:
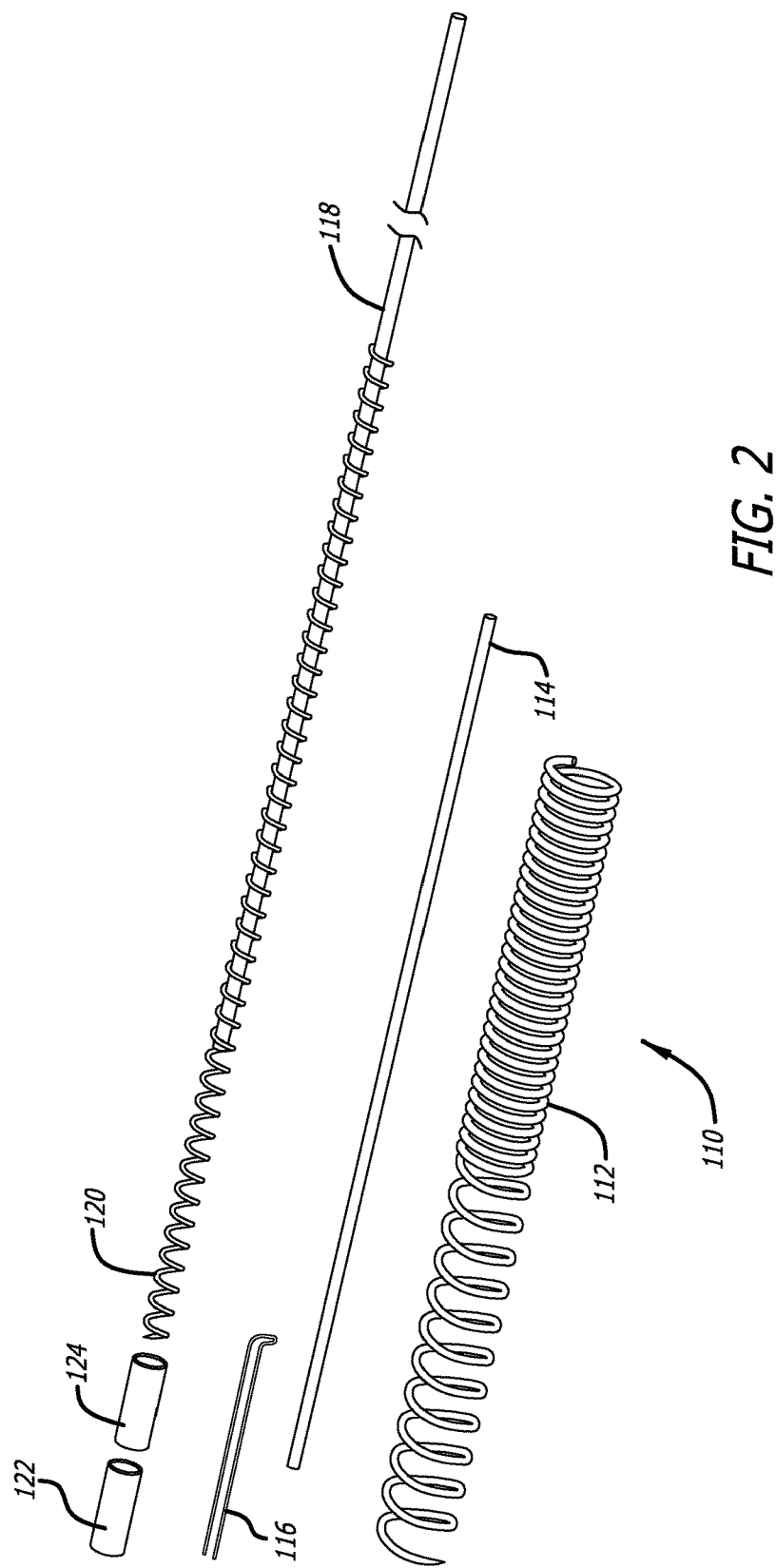
FIG. 2 illustrates an exploded view of a preferred embodiment of a release mechanism according to the present invention.
Figure 3:
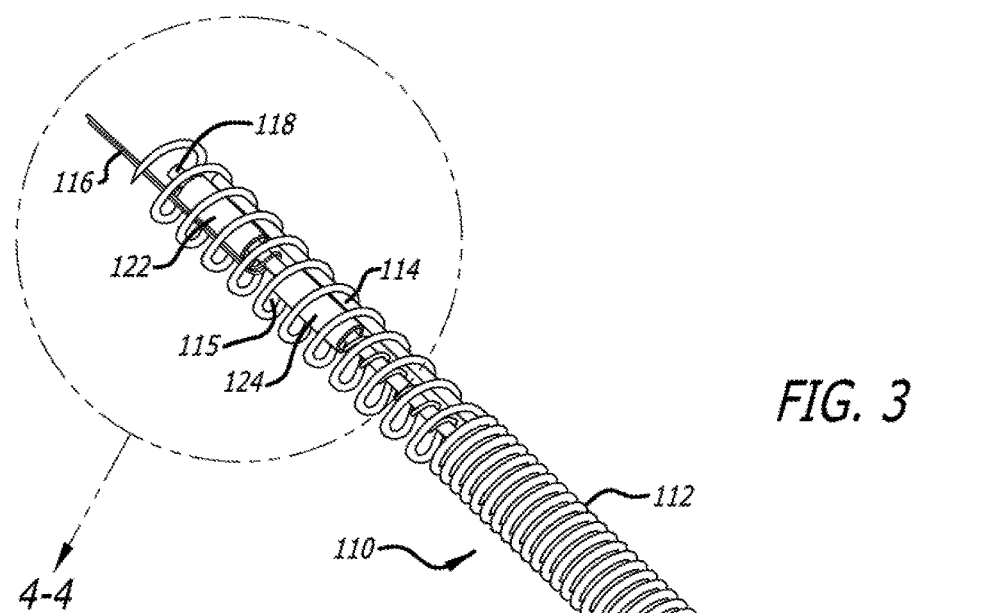
FIG. 3 illustrates an assembled perspective view of the release mechanism of FIG. 2.
Figure 4:
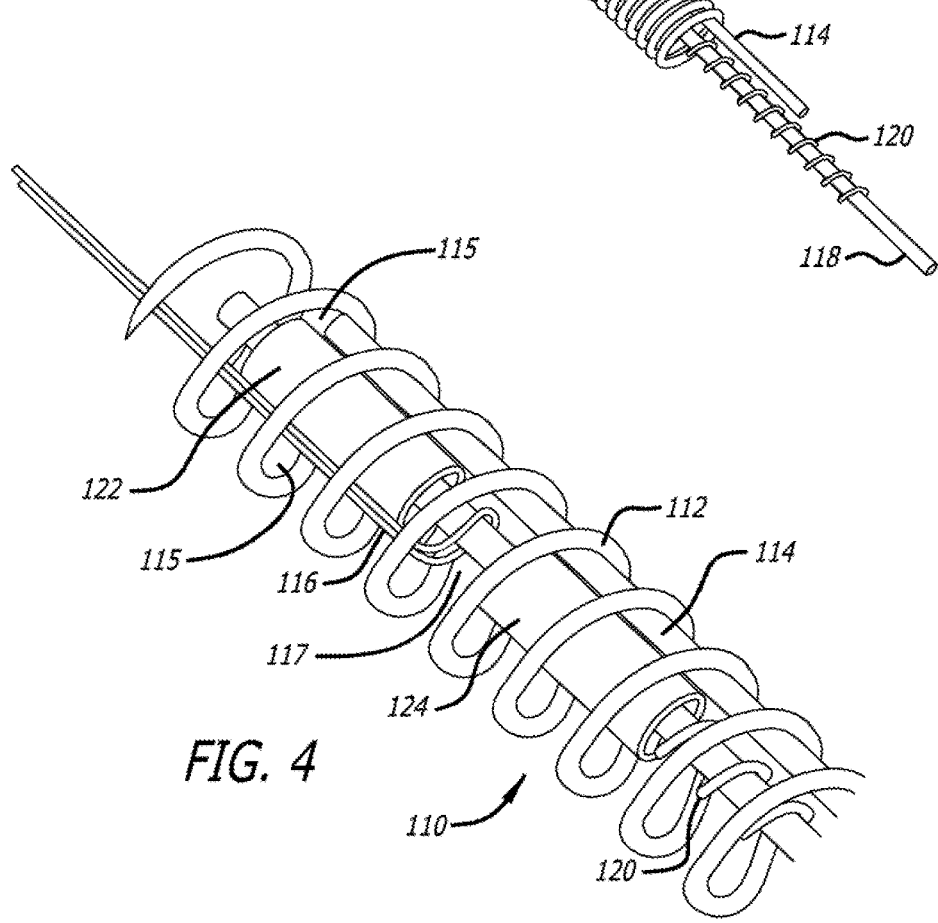
FIG. 4 illustrates an enlarged view of area 4-4 showing the release mechanism of FIG. 3.

FIG. 2 illustrates an exploded view of the release mechanism 110 according to a preferred embodiment of the present invention. FIG. 3 illustrates an assembled view of the mechanism 110, while FIG. 4 illustrates a magnified view of area 4-4.

As explained in further detail below, the release mechanism 110 selectively releases an implantable device 104 by sliding a detachment mandrel 118 to release a tether 116 that is looped around the detachment mandrel 118. More specifically, a free end (e.g., a distal free end) of the mandrel 118 is slid past an opening, free space or aperture located near a distal end of the delivery device 100. The tether 116 is attached to the implantable device 104 (e.g., by adhesive, a knot, clip, etc.). Therefore, when the free end of the detachment mandrel 118 is retracted to a predetermined location (e.g., such that it is exposed or moved past the aperture), the loop of the tether 116 slides off the mandrel 118, releasing the implantable device 104 from the delivery system 100.

Alternately, both ends of the tether 116 can be fixed to the delivery system 100 (e.g., the outer coil 112), positioned through a portion of the implantable device 104 (e.g., a loop or coil), then looped over the mandrel 118. In this respect, the mandrel 118 acts as a sliding or lateral moving latch member.

Preferably, the mandrel 118 is an elongated cylindrical member that extends to the proximal end of the delivery device 100, or is attached to other mechanisms that extend to the distal end of the delivery device 100, thereby allowing control of the mandrel 118 from a user at the proximal end. It should be understood that the mandrel may have a variety of cross sectional shapes, such as circular, square, rectangular and hexagonal. Additionally, this mandrel 118 preferably either extends to the proximal end or the delivery device 100 or mechanically connects to the proximal end to allow a user at the proximal end to manipulate the mandrel 118 and thereby cause the release of the implant.

The release system 110 is at least partially contained within an outer coil 112, which provides support and protection for the release mechanism 110. Preferably, this outer coil 112 is located at the distal end of the body 102; however, it may also be fully or partially embedded in the body 102, an outer sheath or outer layer. The outer coil 112 is preferably composed of a semi-rigid material (e.g., Nitinol, stainless steel, or radiopaque material) to maintain the overall shape of the device, yet flex as it is passed through a patient.

The release system 110 further comprises a distal tube member 122 and a proximal tube member 124, each of which are attached to a support mandrel 114 along their outer surface. Preferably, the tube members 122 and 124 are positioned in line with each other so as to leave a gap or open space 117 large enough for the tether 116 to pass through, as seen best in FIG. 3. The tube members 122 and 124 are preferably sized to fit within the passage of the body 102 (i.e., within coil 112) and are further composed of a rigid or semi-rigid material such as Nitinol or stainless steel. The support mandrel 114 is also preferably composed of a rigid material such as Nitinol or stainless steel and is fixed to the tubes 122, 124 and outer coil 112. The existence of the support mandrel 114 between the tubes 122, 124 and the outer coil 112 creates a radial gap 115 therebetween, through which the tether 116 is longitudinally routed until it enters the open space 117 and accesses the detachment mandrel 118.

The detachment mandrel 118 and the interior passages within the tubes 122 and 124 are sized such that the detachment mandrel 118 can freely move through these passages axially. Preferably, a distal end of the detachment mandrel 118 can further slide at least partially past the gap or open space, exposing the distal end (so that the tether 116 can slide off, releasing the implant 104). In this respect, the tubes 122 and 124 act as a housing for the detachment mandrel 118.

The delivery system 100 also includes an inner coil 120 that acts as a guide or passage for the detachment mandrel 118 as it slides back and forth to release the tether 116 and provides kink resistance. In this respect, the inner coil 120 is disposed around the detachment mandrel 118 and is further fixed to proximal tube 124. The inner coil 120 also includes a different pitch than the outer coil 112 which helps prevent the inner coil 120 from wedging between the loops of the outer coil 112. Preferably, the inner coil 120 is composed of a rigid material such as Nitinol or stainless steel and extends proximally past the outer coil 112 as seen best in FIG. 3.

In operation, the user advances the distal end of the delivery system 100 to a target location within a patient. When the user is satisfied with the placement of the implantable device 104, the implantable device release control 108 is actuated (e.g., the detachment mandrel 118 is pulled proximally), causing the distal end of the detachment mandrel 118 to move in a proximal direction. The distal end of the detachment mandrel 118 moves past the proximal end of distal tube 122, creating a gap between the mandrel 118 and the tube 122. Preferably, the tether 116 is under tensions and therefore immediately slides off the mandrel 118 as soon as the previously mentioned gap opens up. At this point, the implantable device 104 is free from the delivery system 100 and the delivery system 100 can be removed from the patient.

It should be understood that additional delivery controls or options known in the art are possible with the delivery system 100. For example, a sheath can be used over the body 102 to control the expansion of implantable device 104 (e.g., prevents a stent from expanding until the sheath is pulled away from the device 104). In another example, additional lumens containing additional tools or controls are possible.

FIGS. 5-7 illustrate another preferred embodiment of a implantable device release mechanism 130 according to the present invention. Generally, the release mechanism 130 is similar to the previously described release mechanism 110. However, the present release mechanism 130 includes a single tube 132 instead of the two previous tubes 122 and 124.

In the present preferred embodiment, the single tube 132 includes an aperture or cut-away portion 132A. The tether 116 is looped over the detachment mandrel 118 and passes through the cut-away portion 132A. In this respect, as the detachment mandrel 118 is moved proximally by the previously described device release control 108, the looped portion of the tether 116 slides off the detachment mandrel 118 and out the cut-away portion 132A, releasing the device 104.

Preferably, the aperture or cut-away portion 132A can be formed by laser or mechanical cutting of a tube or adhering two tubes together. Also, the cut-away portion 132A preferably includes an angled cut (i.e., an edge surface not at 90 degrees to the length of the tube 132) to prevent rubbing or friction against the tether 116 and thereby minimizing damage to the tether 116. Preferably, at least the distal portion of the aperture 132A has a non 90 degree cut angle (i.e., the portion on which the tether 116 rests). In one example, at least the distal portion of the aperture 132A has a cut angle between about 10 and 80 degrees relative to an axis of the length of the tube 132.

As previously described with regard to release mechanisms 110 and 130, the free ends of the tether 116 can be connected to the delivery device 100 (e.g., coil 112) for procedures when the tether 116 may pose a high risk of complications to a patient. Alternately, the tether 116 may remain with the implant 104 after implantation (i.e., both free ends of the tether are connected to the implant 104) for procedures when the tether 116 may pose a low risk of complications to a patient. The tether 116 either remains in the patient or degrades if composed of a biodegradable material.

Figure 8:
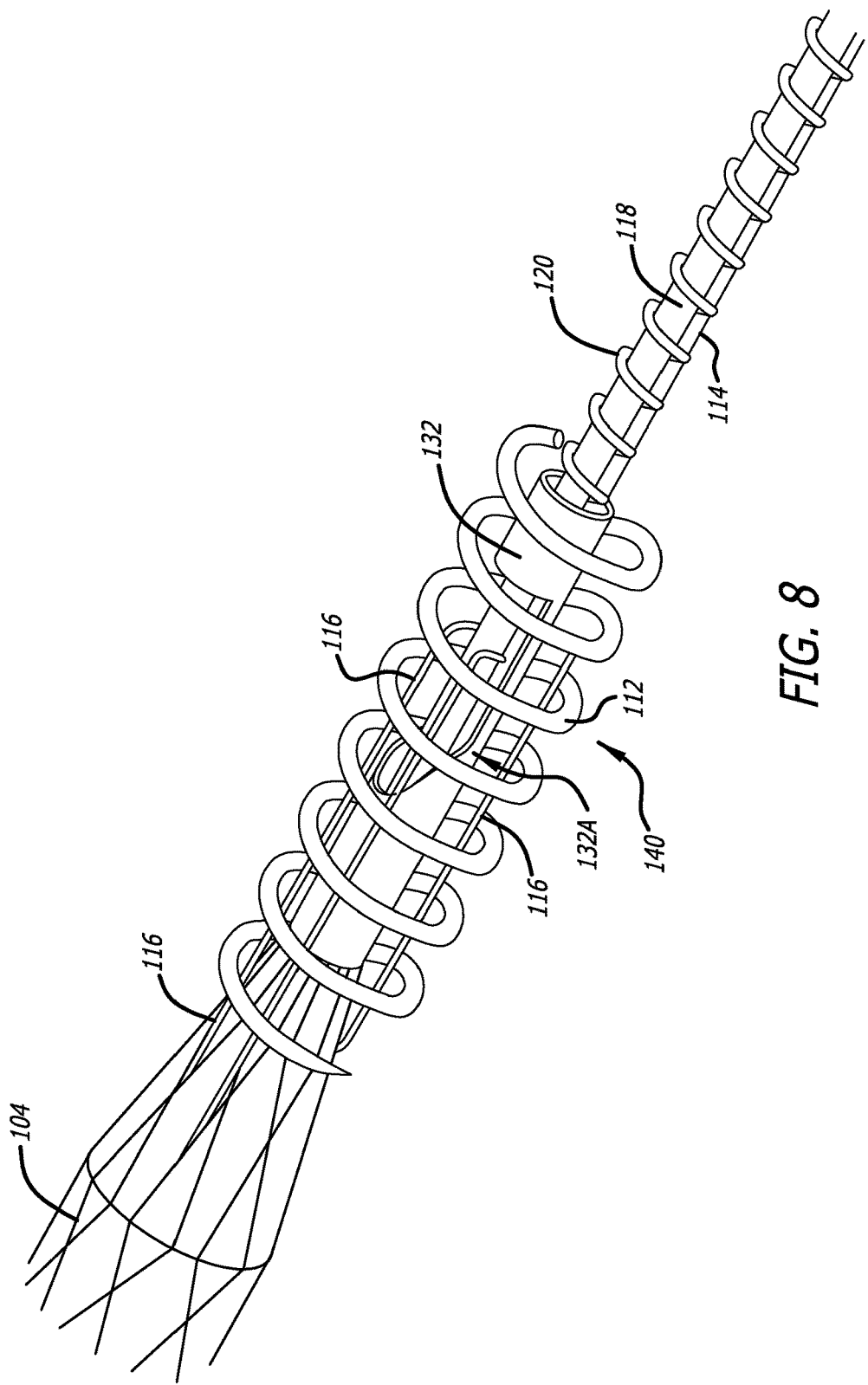
FIG. 8 illustrates a perspective view of another preferred embodiment of a release mechanism according to the present invention.
Figure 9:
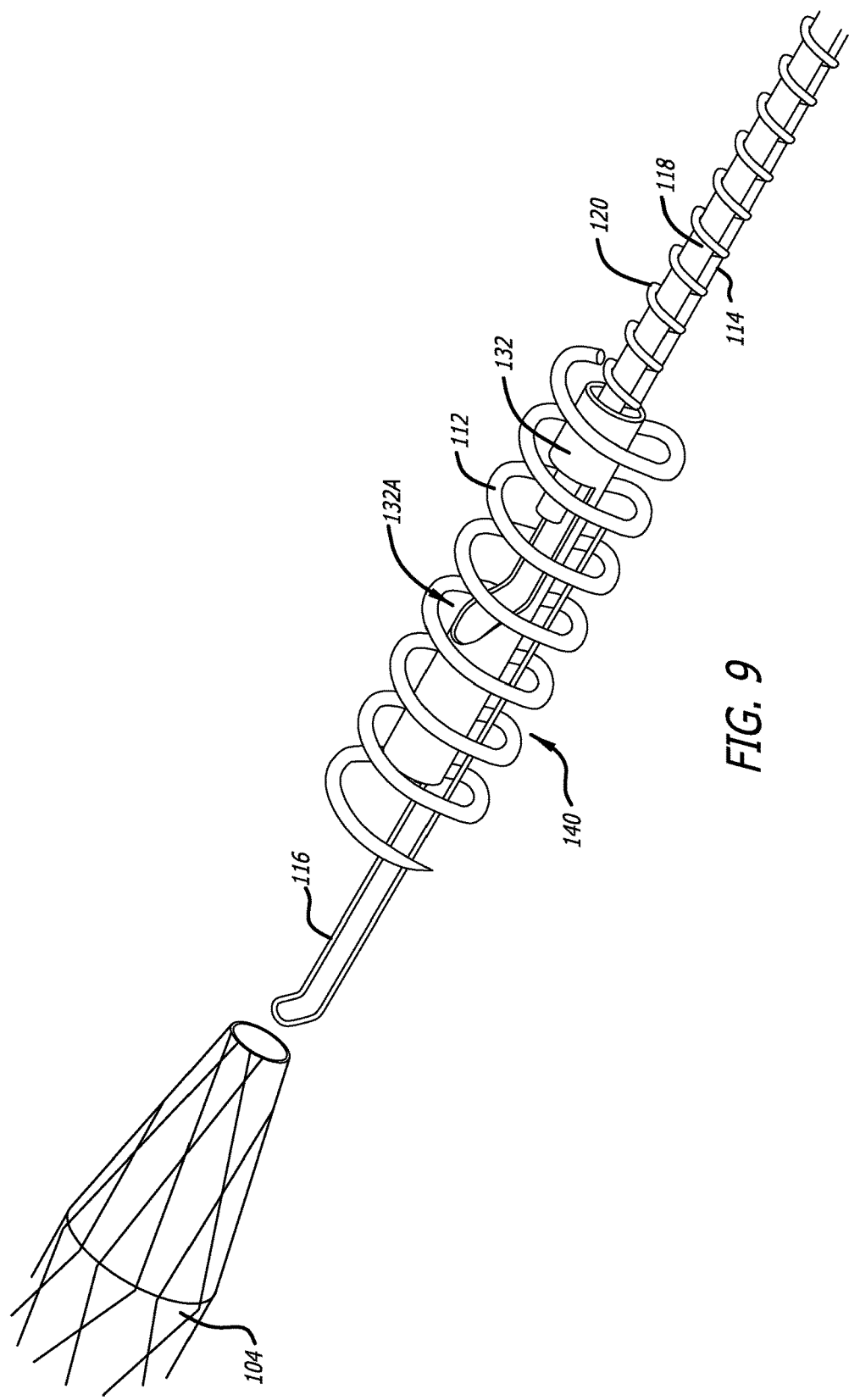
FIG. 9 illustrates a perspective view of the release mechanism of FIG. 8 in a released or deployed configuration.

FIGS. 8 and 9 illustrate an alternative tether configuration as part of another preferred embodiment of a release mechanism 140 according to the present invention. As seen best in the unreleased position of FIG. 8, the free ends of the tether 116 are fixed (e.g., adhesive, tying, or similar methods of fixation) to the outer coil 112. The tether 116 passes through apertures or around spokes or coils of the device 104, then through cut-away portion 132A and around the detachment mandrel 118.

As seen in FIG. 9, when the detachment mandrel 118 moves proximally, the loop portion of the tether 116 slides off the detachment mandrel 118. The tether 116 slides through the device 104, releasing the device 104. In this respect, the tether 126 is removed from the patient with the delivery system 100, preventing the tether 116 from otherwise causing complications in the patient (e.g., blood clots when used with stents). As with the other embodiments, the support mandrel 114 is fixed between the outer coil 112 and the tube 132. The support mandrel also creates a radial gap 115 between the tube 132 and the outer coil 112 through which the tether 116 is longitudinally routed until it enters the open space 132A in the tube 132.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A delivery system for an implant comprising:
an elongated body;
an open inner coil having a first pitch;
an implant capture member associated with said elongated body and movably aligned along said elongated body within said inner coil;
a flexible tether connectable to said implant and at least partially positioned around said implant capture member;
an outer coil disposed around the flexible tether and having an open section with a second pitch that is different than said first pitch so as to prevent interference between said inner coil and said outer coil;
at least one cylindrical member defining an open space providing access to said implant capture member;
a support mandrel fixed between said at least one cylindrical member and said outer coil, said support mandrel connecting said at least one cylindrical member to said outer coil such that a radial position of said cylindrical member within said outer coil is held, thereby maintaining a radial gap between the at least one cylindrical member and the outer coil through which said flexible tether is routed;
said implant capture member being movable in a predetermined direction so as to manipulate said position of said tether and cause release of said implant;
wherein said tether is under axial tension so as to slide off said implant capture member after movement in said predetermined direction.

2. The delivery system of claim 1, wherein said open space is positioned near a distal end of said elongated body through which said tether passes into.

3. The delivery system of claim 2, wherein movement of a free end of said implant capture member past at least a portion of said open space releases said tether from said implant capture member.

4. The delivery system of claim 3, wherein said at least one cylindrical member comprises a first cylindrical member and a second cylindrical member and wherein said open space is formed therebetween.

5. The delivery system of claim 3, wherein said at least one cylindrical member comprises a single cylindrical member and wherein said open space is constituted by an aperture in said cylindrical member.

6. The delivery system of claim 3, wherein said tether comprises a first and second free end, each of which is fixed to said implant.

7. The delivery system of claim 3, wherein said tether comprises a first and second free end, each of which is coupled to said elongated body.

8. A delivery system for an implant comprising:
an elongated body;
an implant release mechanism disposed near a distal end of said elongated body, said implant release mechanism comprising an actuating member slidably disposed within an inner coil disposed within said elongated body;
a flexible tether connectable to said implant and to said actuating member so as to be under axial tension and to hold said implant to said elongated body;
an outer coil disposed around said flexible tether, said outer coil having an open section with a pitch that differs from a pitch of said inner coil;
at least one housing member defining a space through which said flexible tether passes to engage with said actuating member;
a support mandrel fixed between said at least one housing member and said outer coil, maintaining a radial gap between the at least one housing member and the outer coil through which said flexible tether is routed;
said actuating member being slidable in a predetermined axial direction such that said tether is released from holding said implant to said elongated body.

9. The delivery system of claim 8 wherein said at least one housing member comprises a first housing member having a first passage and a second housing member having a second passage, said first housing member and said second housing member spaced apart from each other; wherein said actuating member is slidably disposed within said first housing member and said second housing member.

10. The delivery system of claim 8 wherein said at least one housing member comprises a single housing member having a passage therethrough and an aperture located in a wall of said first housing; wherein said actuating member is slidably disposed within said single housing member.

11. The delivery system of claim 10, wherein said aperture comprises a distal portion having a cut angle between 10-80 degrees relative to an axis of a length of said single housing member.

12. The delivery system of claim 8, further comprising an actuation mechanism located near a proximal end of said elongated body for axially moving said actuating member.

13. The delivery system of claim 8 wherein said at least one housing member comprises a single housing member; wherein said actuating member has a first position in which a distal end of said actuating member is covered by said single housing member and a second position in which said distal end of said actuating member is uncovered by said single housing member.

14. The delivery system of claim 13, wherein said tether further comprises a first free end and a second free end, each of which is fixed to said delivery system.

15. The delivery system of claim 13, wherein said tether further comprises a first free end and a second free end, each of which is fixed to said implant.

16. A method of releasing an implant comprising:
providing a delivery system attached to said implant with an axially-tensioned flexible tether and sized for advancement through a vascular system and surrounded by an open outer coil that protects said tether;
actuating a release control on a proximal end of said delivery system; and,
slidably retracting an actuating member so as to release said tether from said actuating member, said actuating member sliding within an open inner coil having a pitch that differs from a pitch of said open outer coil to prevent said inner coil from interfering with said outer coil;
wherein said tether is routed longitudinally within said outer coil through a radial gag between said outer coil and a tubular housing surrounding said actuating member, said radial gap created by a support mandrel connecting said outer coil to said tubular housing.

17. The method of claim 16, wherein said slidably retracting an actuating member further comprises exposing a distal end of said actuating member.

18. The method of claim 16, wherein said slidably retracting an actuating member results in sliding a looped portion of said tether off of said actuating member.

19. The method of claim 18, wherein said retracting an actuating member further comprises exposing a distal end of said actuating member from an opening of said housing.

20. The method of claim 19, further comprising maintaining a connection of at least a portion of said tether to said delivery system.

* * * * *